US00PP36354P3

(12) United States Plant Patent
Schoone

(10) Patent No.: US PP36,354 P3
(45) Date of Patent: Dec. 31, 2024

(54) ***PHALAENOPSIS* PLANT NAMED 'Carajillo'**

(50) Latin Name: *Phalaenopsis hybrida*
Varietal Denomination: Carajillo

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,156

(22) Filed: Apr. 2, 2024

(65) Prior Publication Data

US 2024/0334853 P1 Oct. 3, 2024

Related U.S. Application Data

(60) Provisional application No. 63/456,505, filed on Apr. 2, 2023.

(51) Int. Cl.
*A01H 6/62* (2018.01)
*A01H 5/02* (2018.01)

(52) U.S. Cl.
USPC ..... Plt./311
CPC ..... *A01H 6/62* (2018.05)

(58) Field of Classification Search
USPC ..... Plt./263.1, 311
See application file for complete search history.

(56) References Cited

U.S. PATENT DOCUMENTS

PP33,553 P2 * 10/2021 Van Swieten ..... Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'Carajillo', characterized by its upright plant habit; moderately vigorous growth habit; strong flowering stems; strong leaves; freely flowering habit with typically two inflorescences developing per plant, each inflorescence with numerous flowers; flowers with purplish pink-colored petals with a few fine purplish red-colored dots towards the base; and good postproduction longevity.

2 Drawing Sheets

Figure 1:
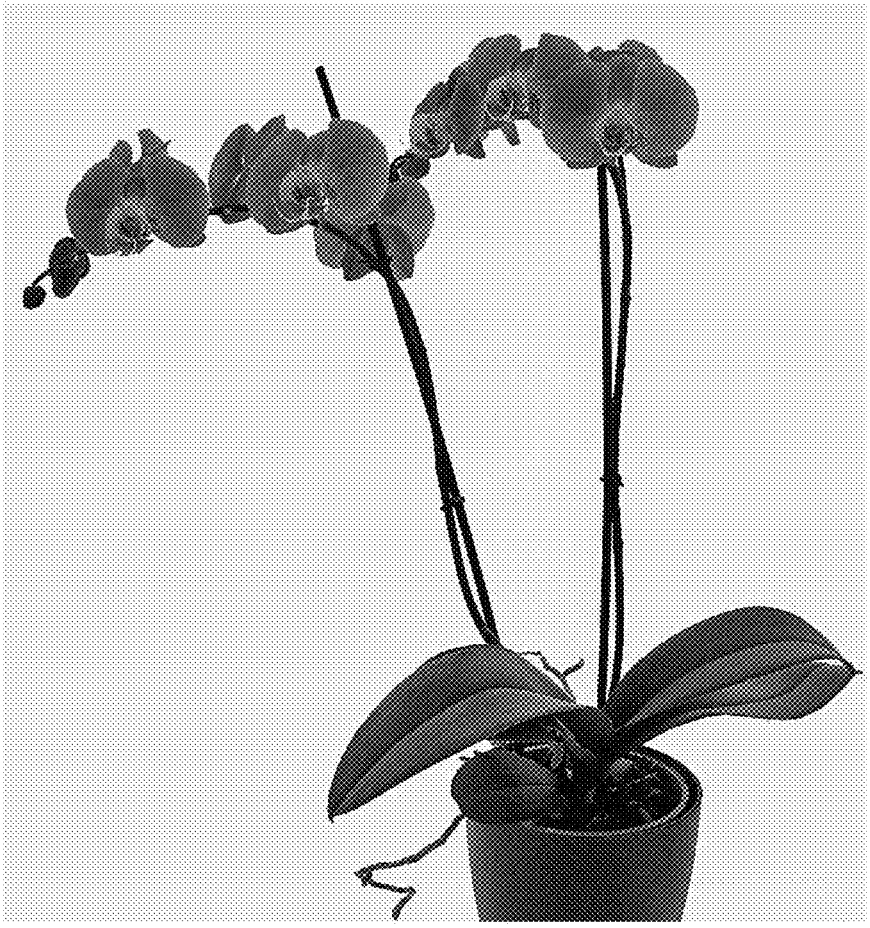

Botanical designation: *Phalaenopsis hybrida.*
Cultivar denomination: 'CARAJILLO'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Feb. 27, 2023, application number 2023/0513. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102 (b) (1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida,* and hereinafter referred to by the name 'Carajillo'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in February 2013 in De Lier, The Netherlands of a proprietary selection of *Phalaenopsis hybrida* identified as Flori donker, not patented, as the female, or seed, parent with a proprietary selection of *Phalaenopsis hybrida* identified as code number GE944, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November 2019.

Asexual reproduction of the new *Phalaenopsis* plant by in vitro meristem propagation in a controlled environment in Assendelft, The Netherlands since November 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Carajillo'. These characteristics in combination distinguish 'Carajillo' as a new and distinct *Phalaenopsis* plant:

1. Upright plant habit.
2. Moderately vigorous growth habit.
3. Strong flowering stems.
4. Strong leaves.
5. Freely flowering habit with typically two inflorescences developing per plant, each inflorescence with numerous flowers.
6. Flowers with purplish pink-colored petals with a few fine purplish red-colored dots towards the base.
7. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals of plants of the new *Phalaenopsis* have a few fine purplish red-colored dots towards the base whereas flower petals of plants of the female parent selection do not have any dots.
2. Cirrhose tips of the labellum of plants of the new *Phalaenopsis* are longer than cirrhose tips of the labellum of plants of the female parent selection.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* have a few fine purplish red-colored dots towards the base whereas flower petals of plants of the male parent selection do not have any dots.
2. Lateral lobes of the flower labella of plants of the new *Phalaenopsis* are mostly white in color whereas lateral lobes of the flower labella of plants of the male parent selection are purplish red in color.

Plants of the new *Phalaenopsis* can be compared to plants of *Phalaenopsis hybrida* 'Midsummer Night', not patented. In side-by-side comparisons, plants of the new *Phalaenopsis* differ primarily from plants of 'Midsummer Night' in the following characteristics:

1. Flower petals of plants of the new *Phalaenopsis* have a few fine purplish red-colored dots towards the base whereas flower petals of plants of 'Midsummer Night' do not have any dots.
2. Lateral lobes of the flower labella of plants of the new *Phalaenopsis* are mostly white in color whereas lateral lobes of the flower labella of plants of 'Midsummer Night' are purplish red in color.
3. Cirrhose tips of the labellum of plants of the new *Phalaenopsis* are longer than cirrhose tips of the labellum of plants of 'Midsummer Night'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet FIG. 1 is a side perspective view of a typical flowering plant of 'Carajillo' grown in a container.

Figure 2:
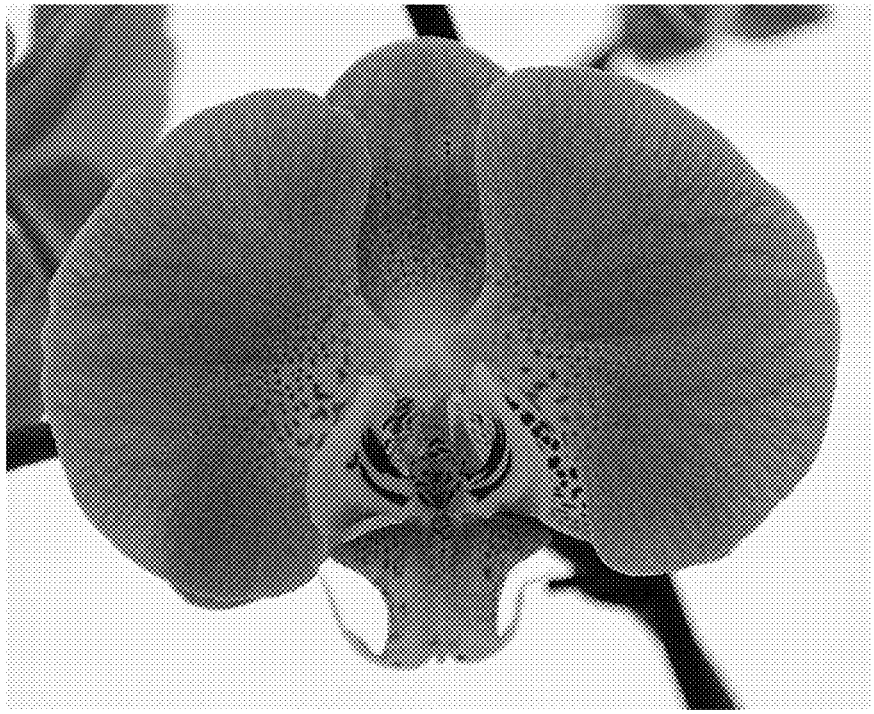

The photograph on the second sheet FIG. 2 is a close-up view of a typical flower of 'Carajillo'.

DETAILED BOTANICAL DESCRIPTION

The aforementioned photographs and following observations and measurements describe plants grown during the winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Carajillo'.

Parentage:

*Female, or seed, parent*.—Proprietary selection of *Phalaenopsis hybrida* identified as Flori donker, not patented.

*Male, or pollen, parent*.—Proprietary selection of *Phalaenopsis hybrida* identified as code number GE944, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 13 cm.

*Plant height, substrate level to top of floral plane*.—About 47.3 cm.

*Plant diameter or spread*.—About 33.2 cm.

Leaf description:

*Arrangement and quantity*.—Distichous, simple; sessile; about three fully-developed leaves per plant.

*Length*.—About 19.5 cm.

*Width*.—About 7.1 cm.

*Aspect*.—Semi-erect to horizontal and eventually outwardly arching.

*Shape*.—Narrowly elliptic-oblong to narrowly obovate; slightly carinate and apex moderately reflexed.

*Apex*.—Unequal broadly acute.

*Base*.—Sheathing. Sheath length: About 1.9 cm. Sheath width: About 1.3 cm. Sheath color: Close to 143A with upper margins, close to NN137A.

*Margin*.—Entire; not undulate.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to NN137B. Developing leaves, lower surface: Close to a blend of NN137B and 146A; towards the margins, strongly tinged with close to 200A. Fully expanded leaves, upper surface: Close to NN137B; venation, close to NN137A. Fully expanded leaves, lower surface: Close to a blend of 137B and 146A; towards the margins, close to NN137B; venation, close to NN137B tinged with close to 200A.

Inflorescence description:

*Appearance and flowering habit*.—Showy zygomorphic flowers arranged on axillary simple or branched racemes; typically two inflorescences develop per plant; each inflorescence with about ten open flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 20.3 cm.

*Inflorescence width*.—About 13.4 cm.

*Flower buds*.—Height: About 1.6 cm. Diameter: About 1.4 cm by 1.7 cm. Shape: Broadly ovate. Color: Close to 152C; towards the base, close to 151A and towards the apex, strongly tinged with close to 176A.

*Flower size*.—About 7.2 cm (vertical) by 8.3 cm (horizontal).

*Flower depth*.—About 3.7 cm.

*Petals, quantity and arrangement*.—Three, two lateral petals and one center petal transformed into a labellum.

*Lateral petals*.—Length: About 3.9 cm. Width: About 5.5 cm. Shape: Broadly deltoid-reniform to close to lunate. Apex: Rounded, irregular. Margin: Entire to very shallowly angulate; not undulate. Texture and luster, upper and lower surfaces: Smooth, glabrous; moderately velvety; matte. Color: When opening, upper surface: Close to 186B; towards the center, close to 185C and 185D; towards the margins, close to 70B; at the apex and narrow edges, tinged with close to 145B and 145C; at the base, close to 145D and 157C with dots, close to 71A. When opening, lower surface: Close to 186C and 186D; towards the center, close to 195B; at the apex and narrow edges, tinged with close to 145C and 145D; at the base, close to 145D; and venation, close to 186B and 185C. Fully opened, upper surface: Close to N74C and N74D; towards the margins, close to 75A; at the apex, slightly tinged with close to 75D; narrow edges, close to 196D; at the base, close to NN155B with dots, close to 72A; colors do not change with subsequent development. Fully opened, lower surface: Close to 75A and 75B; towards the center and apex, tinged with close to 196A; narrow edges, close to 196D; venation, close to N74C; colors do not change with subsequent development.

*Labella*.—Appearance: Three-parted with two lateral lobes and a central lobe. Length, lateral lobes: About 2.2 cm. Width, lateral lobes: About 1.6 cm. Length, central lobe: About 2.2 cm. Width, central lobe: About 1.1 cm to 2.2 cm. Length, cirrhose tips: About 1.5 cm. Shape, lateral lobes: Obovate. Shape, central lobe: Broadly oblong. Apex, lateral lobes: Obtuse. Apex, central lobe: Cleft with two upwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 6 mm in height. Color: When opening, upper surface: Lateral lobes: Close to NN155D; lower half, slightly flushed with close to 76C; lower margin, close to 10C and edge, tinged with close to 187B; at the base, axial stripes, close to 187B. Central lobe: Close to 76D with marbling and fine dots, close to 71C and 71D; basal lobes, close to 162A and 162B; fine dots, close to 71B and 71C; towards the apex and cirrhose tips, close to NN155A and NN155B; fine stripes, close to 71A; at the base, close to NN155D with radial stripes, close to 183A. When opening, lower surface: Lateral lobes: Close to NN155B; lower half, slightly flushed with close to 76C; lower margin, close to 10C and edges, tinged with close to 187B; at the base, axial stripes, close to 187B. Central lobe: Close to 75A and 75B; margins of basal lobes, close to 175C; at the apex and cirrhose tips, close to 155A; at the base, close to 195A; and midvein, close to 195B. Fully opened, upper surface: Lateral lobes: Close to NN155D; lower half, slightly flushed with close to 76C; lower margin, close to 10C and edge, tinged with close to 187B; at the base, axial stripes, close to 187B. Central lobe: Close to 76D with marbling and fine dots, close to 71B and 71C; basal lobes, close to 162A and 162B; fine dots, close to 71A and 71B; towards the apex and cirrhose tips, close to NN155A and NN155B; fine stripes, close to 71A; at the base, close to 157D with radial stripes, close to 183A. Fully opened, lower surface: Lateral lobes: Close to NN155B; lower half, slightly flushed with close to 76C; lower margin, close to 9C and edges, tinged with close to 187B; at the base, axial stripes, close to 187B. Central lobe: Close to 75A and 75B; margins of basal lobes, close to 175C; at the apex and cirrhose tips, close to 155A; at the base, close to 195A; and midvein, close to 195B. Callosities: When developing, inner surface: Close to 154A with fine dots and stripes, close to 183A. When developing, outer surface: Close to NN155A. Fully developed, inner surface: Close to 13B with fine dots and stripes, close to 183A. Fully developed, outer surface: Close to NN155B with stripes, close to 183A.

*Sepals*.—Quantity and arrangement: Three, one upper dorsal sepal and two lower lateral sepals. Length, dorsal sepal: About 3.8 cm. Width, dorsal sepal: About 2.9 cm. Length, lateral sepals: About 3.8 cm. Width, lateral sepals: About 2.6 cm. Shape, dorsal sepal: Ovate. Shape, lateral sepals: Ovate to broadly ovate. Apex, dorsal sepal: Bluntly acute. Apex, lateral sepals: Broadly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 185C; towards the apex, tinged with close to 196B; at the base, densely and finely dotted, close to 160C; venation, close to 186A and 186B. When opening, lower surface: Close to 185C; towards the center, strongly tinged with close to 152C and 152D. Fully opened, upper surface: Close to N74C and N74D; towards the margins, close to 75A; towards the apex, slightly tinged with close to 75D with narrow edges, close to 196D; towards the base, close to NN155B and at the base and center, fine dots, close to 72A; venation, close to 186B. Fully opened, lower surface: Close to a blend of N78C and 186C; towards the center, tinged with close to 195B; venation, close to 186A and 186B. Color, lateral sepals: When opening, upper surface: Distally, close to 185B and 185C; proximally, close to 150B and 150C; densely and finely dotted, close to 185A and 187C. When opening, lower surface: Close to 184B and 184C; at the centers, close to N144D. Fully opened, upper surface: Distally, close to N74C and N74D; proximally, close to 154D; densely and finely dotted, close to 185A and 187C. Fully opened, lower surface: Close to 186B; at the centers, close to 145B.

*Peduncles*.—Length: About 49.5 cm. Diameter: About 6 mm. Strength: Strong. Aspect: Upright to outwardly arching. Texture and luster: Smooth, glabrous; matte. Color: Close to 200A with fine dots, close to 150C.

*Pedicels*.—Length: About 4 cm. Diameter: About 3.5 mm. Strength: Moderately strong. Aspect: About 75° from peduncle axis. Texture and luster: Smooth, glabrous; matte. Color: Close to 146C; proximally, strongly tinged with close to 183A and distally, tinged with close to 182C.

*Reproductive organs*.—Androecium: Column length: About 8 mm. Column width: About 5.5 mm. Column color: Close to N155B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 157D. Ovary length: About 1 cm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Carajillo' as herein illustrated and described.

* * * * *